United States Patent [19]
Curri

[11] Patent Number: 6,013,277
[45] Date of Patent: *Jan. 11, 2000

[54] COMPOSITIONS FOR TOPICAL TREATMENT OF ERECTILE IMPOTENCE

[75] Inventor: Sergio Curri, Milan, Italy

[73] Assignee: Inpharma S.A., Lugano, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,228

[22] PCT Filed: Jul. 25, 1995

[86] PCT No.: PCT/IB95/00584

§ 371 Date: Mar. 8, 1996

§ 102(e) Date: Mar. 8, 1996

[87] PCT Pub. No.: WO96/03991

PCT Pub. Date: Feb. 15, 1996

[30] Foreign Application Priority Data

Aug. 5, 1994 [CH] Switzerland ............................. 2454/94
Dec. 16, 1994 [CH] Switzerland ............................. 3809/94

[51] Int. Cl.$^7$ ................................................. A61K 9/127
[52] U.S. Cl. .............................. 424/450; 514/25; 514/27; 514/937; 514/944; 514/969
[58] Field of Search ............................. 424/450; 516/25, 516/27; 514/78, 937, 944, 969

[56] References Cited

U.S. PATENT DOCUMENTS

5,256,652  10/1993  El-Rashidy ................................. 514/58
5,482,039  1/1996  Place .................................... 128/653.1

FOREIGN PATENT DOCUMENTS

0459377  12/1941  European Pat. Off. .
4125255  2/1993  Germany .
9503787  2/1995  WIPO .

OTHER PUBLICATIONS

*The Merck Index*, Tenth Edition, p. 1397.
*International Drug Directory*, 16th Edition, p. 1272.
S. Budavari, ed., et al., *The Merck Index*, 11th Edition, 1989, p. 1539.

Lymphology (United States), Mar. 1993, vol. 26, No. 1 pp. 25–27, Casley–Smith, Jr. et al., 'Topical treatment of acute hindlimb lymphedema of the rat using a troxerutin–phosphatidycholine complex in liposomal–like microdispersion,' see the whole document.

Br. J. Clin. Pract. (United Kingdom), 1993, vol. 47, No. 3 pp. 118–119, Riley A.J. 'Local pharmacotherapy for impotence' see the whole document.

Drugs (New Zealand), 1992, vol. 44, No. 6, pp. 1013–1032, 'Hydroxyethylrutosides; A review of its pharmacology, and therapeutic efficacy in venous insufficiency and related disorders'(see abstracts).

Drugs Exp. Clin. Res. (Switzerland), Jul. 1993 vol. 42, No. 9 pp. 627–31, Otomo S. et al., 'Prostaglandin El incorporated in lipid microspheres (lipo PG1), '(see the whole document).

Urology (United States), Jul. 1993 vol. 42, No. 1 pp. 73–75, Wolfsen B. et al, 'Intraurethral prostaglandin E–2 cream; a possible alternative treatment for erectile dysfunction. '(see the whole document)

Database WPI Week 8606, Derwent Publications Ltd., Long, GB; AN 86–039687 & JP, A,60 260 524 (Nakanashi M.) 23 Dec. 1985 (see abstract).

J. of Urology, vol. 153, Apr. 1995 p. 474A Canning J R et al., 'Prostaglandin El as a topical agent for treatment of erectile dysfunction'(see abstract).

J. Urol (United States), Jun. 1995, vol. 153, No. 6 pp. 1828–30, Dysfunction 'Topical prostaglandin–El for the treatment of erectile'(see the whole document).

*Primary Examiner*—Gollamudi S. Kishore
*Attorney, Agent, or Firm*—Ladas & Parry

[57] ABSTRACT

Description of pharmaceutical or cosmetic compositions aimed at improving the local microcirculation of the penis for chronic topical treatment of vascular impotence due to vascular causes, with main impairment of the arterial-arteriolar afferents of the cavernous bodies. The new pharmacological properties of the complex between PGE1 and/or Troxerutine with Phosphatidylcholine are administered locally on the skin of the penis; the activity is obtained using the T.E.B. system according to Curri.

20 Claims, No Drawings

COMPOSITIONS FOR TOPICAL TREATMENT OF ERECTILE IMPOTENCE

This application is a 371 of PCT/IB95/00584 filed Jul. 25, 1995.

This invention refers in general to pharmaceutical or cosmetic compositions aimed at improving local microcirculation of the penis in conditions such as erectile impotence of vascular origin in which the cause of the dysfunction is attributable to a deficiency in blood flow to the cavernous bodies.

The invention more specifically refers to pharmaceutical and/or cosmetic compositions able to increase the volume and speed of blood flow in the capillary network of the skin that covers the penis and of the mucosa of the glans penis.

It is known that during the last few years the pathogenetic question as to the real cause of erectile impotence has continued to place ever increasing emphasis on the vascular origin of the problem rather than on the psychological causes. This is due to the continuous improvement of the instrumental techniques available for diagnosis. In a consistent number of cases of impotence it is, therefore, now possible to identify the organic (and not simply functional) origin of the affliction.

This obviously means that medical treatment of impotence reverts less to psychotherapy, favouring drugs or methods that enable adequate treatment of local vascular deficiencies.

It is also known that the various types of impotence due to vascular problems are presently classified in the two following forms:

1. arterial forms, in which there is impairment of the arterial afferents to the penile cavernous bodies;
2. venous forms, in which there is impairment of the venular-venous efferents of the cavernous bodies and the system's collector veins.

Whilst it is possible to treat the latter types of impotence, also referred to as "from venous leakage", with fine vascular surgery to reduce the quantity of blood that flows away from the cavernous bodies, therapeutical measures for the former types are scarce and restricted to provoking a pharmacological erection by intracavernous injection of vasodilators such as papaverine and, more recently, prostaglandins or prostacyclins. Intracavernous injection of these substances causes a temporary erection by blocking the efferent routes of exit for the blood that flows into the cavernous bodies. This approach achieves the desired effect, but does not treat the primary causes of the erectile deficiency. It, therefore, represents a temporary therapeutical measure, to be adopted as required, but which is not followed by a progressive improvement of the underlying pathological erectile condition that is at the basis of the problem. The results are, therefore, partial, of limited duration and, as such, unsatisfactory.

Topical medications, containing papaverine, in the form of ointments or gels for local application on the penis in cases of erectile impotence, have recently been proposed. The results are disappointing, since papaverine administered topically does not, in any of the cases, cross the tunica albuginea of the penis nor penetrate directly into the cavernous bodies. The use of nitrates and nitrites also, as such in the form of ointments, gels, or transdermal plasters, has not led to the expected results.

The problem at the basis of this invention, therefore, is to find and make available a pharmaceutical or cosmetic composition able to increase the speed and volume of blood flow in the small arteries and pre-capillary arterioles, especially the small terminal branches of the helicine arteries which lead into the penile cavernous bodies, as well as into the capillaries of the penis skin and the mucosa of the glans penis.

According to this invention, instead of prostacyclins or vasodilators which paralyze the sphygmic activity and the intrinsic tone of the smooth muscle cells of the small arteries, this problem is solved by topical administration of a composition containing a drug with microvasculo-kinetic activity, and, therefore, is able to strengthen the sphygmic activity of the small arteries and consequently the blood volume that reaches the cavernous bodies and the capillaries of the penis within a unit of time. In this manner, opposition is made to the pathological deficiency of the "pumping function" of the small arteries that is present in arterial hypertension and in diabetic and arteriolosclerotic microangiopathy, which are the main causes of penile erectile impotence and/or rapid detumescence of the erected penis.

It is widely known from the data reported in worldwide literature on the subject, that Prostaglandin E1 (PGE1) is an endogenous substance that exerts a wide spectrum of pharmacological activities, among which: increased blood flow due to vasodilation, improved microcirculation due to increased erythrocyte deformability, inhibition of platelet activation and aggregation, inhibition of neutrophil leukocyte activity, increased fibrinolytic activity. Its main indications regard treatment by intra-arterial or intravenous infusion of obliterating peripheral arteriopathies in which the vasodilating action of PGE1 is mainly exploited.

More recently, the relaxing effects of PGE1 on the smooth muscles were exploited in the treatment of erectile impotence of vascular origin, by intracavernous administration of doses varying between 5 to 20 mcg and over, which induce an erection within 2–15 minutes (mean 7.5), lasting between 30 minutes and 7 hours (mean 2.3 h), according to data reported by R. Hasun and W. Stackl ("Prostaglandin E1 test in the diagnosis of vascular impotence", 1er *Symposium Int. sur l'Erection Pharmacologique*, Paris, 17–18 November 1989). The most widespread opinion on the mechanism of action of PGE1 is reported by M. Sohn, R. Sikora and D. Albrecht in: "Comparative study of papaverine and Prostaglandin E1 in diagnosis of venous leakage in erectile dysfunction", *Artéres et Veines* 1991, Vol. X, nr. 4, 263–265: "In contrast to Papaverine or Phentolamin, Prostaglandin E1 has a dualistic action: it effects a direct smooth muscle relaxation of the corpus cavernosum and at the same time inhibits adrenergic activity". This opinion, unanimously shared in international andrological environments, is based on observations made by H. Hedlund and K. E. Anderson, who were the first to describe such effect ("Contraction and relaxation induced by some prostanoids in isolated human penile erectile tissue and cavernous artery", *J. Urol.* 1985, 184, 1245).

The vasodilating effect can be demonstrated also after intraurethral administration ("Medicated Urethral System for Erection", MUSE): administration of high doses of PGE1 (500 mcg) through this route, "effectively produced intracorporal smooth muscle relaxation comparable to intracavernosal injection of PGE1 (10 mcg) . . . furthermore, arterial dilation appeared to be more diffused compared to ICI (H. Padma-Nathan et al, "Hemodynamic effects of intraurethral alprostadil: the medicated urethral system for erection (MUSE)", *Int. J Impotence Res.*, 1994, 6, Suppl. 1).

It has also been observed that a drug normally used for oral treatment of chronic venous insufficiency of the lower limbs, 3-O-beta-hydroxyethylrutine (Troxerutine), applied locally on the penis and glans penis, through appropriate methods and at suitable doses, in patients affected by erectile impotence of vascular genesis, is able to significantly increase the volume and speed of blood flow in the capillary networks of the dorsal and ventral penile areas and of the glans penis, subjected to treatment.

In particular it is believed that Troxerutine—in the form indicated by this invention, i.e.: a physical-chemical complex with Phosphatidylcholine microdispersed in water and, therefore, "liposomal-like"—is able to penetrate deeply and with unique efficacy in every minimum interstice of penile skin and mucosa, involving and significantly increasing the sphygmic function of the small arteries and pre-capillary arterioles of the penis.

In fact, in subjects affected by erectile impotence of vascular origin, it has been observed that the pharmacological stimulus achievable with the compositions of this invention is followed by a statistically significant increase in vasomotility of the small penile arteries and by a rapid and intense increase in the number of perfused capillaries.

For the purposes of this invention, preference is given to the 3-O-beta-hydroxyethyl-rutoside, of vegetable extractive origin that appears as a very fine, yellow-greenish powder with a characteristic odour.

Furthermore, in accordance with this invention, Troxerutine and Phosphatidylcholine purified from Soya are complexed in a molar ratio of 2:1, giving place to a pharmaceutical or cosmetic composition according to known methods.

The compositions of the invention are specified in the claims listed below. Phosphatidylcholine is a group of compounds described i.a. in Documenta Geigy, 7th ed., p. 370 and 371.

Topical application on penile skin of a complex of highly purified Phosphatidylcholine (PC) and PGE1 has surprisingly demonstrated the existence of a pharmacological activity to date not described in the literature available on PGE1. It consists of a microvasculokinetic action, characterized by marked and significant potentiation of the sphygmic activity of the small arteries and pre-capillary arterioles.

This effect appears with criteria that are instrumentally observable within 15–30 minutes from the topical T.E.B. ("Trans-Epidermal Barrier" according to Curri) application of the PC/PGE1 complex. The complexed PGE1 dose that is active on the arterial-arteriolar inotropy, strengthening the sphygmicity of the small arteries and pre-capillary arterioles (see S. B. Curri: "Vasomotility, Sphygmicity and Vasomotion", *Progr. in Appl. Microcirculation*, Karger (Basle) 1993, 20, 8–13; "Vasomotion and Vasomotiity: two different concepts", 16*th World Congr. Int. Union of Angiology, Paris*, Sep. 13–18, 1992, Abstr. Book IL091-1010:226), is between 5 and 100 mcg of the complex that is the subject matter of this invention.

The difference, which is determinant with the knowledge acquired to-date, consists in the fact that the PC/PGE1 complex does not exert a vasodilating effect, but surprisingly activates and strengthens sphygmic contractility of the small arteries and pre-capillary arterioles, thus inducing an increase in the speed and volume of flow in the affluent capillary networks.

The method adopted in order to demonstrate the new activity which is the subject of this invention involves the instrumental evaluation of sphygmic contractility of the small penile arteries and pre-capillary arterioles through computerized calculation of the extension of the sphygmic waves (HFRV="High Frequency Rhythmic Variations"), recorded with a laser-Doppler device (Pf2b, Perimed, Linkoeping, Sweden). Before recording the measurements a calibration was carried out towards the "motility standard" supplied by the manufacturer for a signal between 240–260 PU; the gains of the device were regulated so as to make 1 PU correspond with 10 mV. The values were obtained using "Perisoft" software (Perimed, Linkoeping, Sweden) and statistically analyzed with the two route variance analysis ("Statgraphics Plus") using a computer connected to the recording system.

The material used consisted of 15 male subjects aged between 29 and 64 years, affected by impotence of vascular origin, with significantly impaired microcirculation (see Table 1). The recordings were carried out in a controlled temperature environment, at baseline and 15–30 minutes after topical T.E.B. administration of the PC/PGE1 complex.

The results summarized in Table 1 indicate that the effect on arterial-arteriolar sphygmicity occurred in 100% of the cases observed, with a significant (P=0.005) increase in the mean values related to increased sphygmic motility which passed from 54.33±37.89 mV at baseline to 153±121.6 after application of the PC/PGE1 complex, which is the subject matter of this invention.

TABLE 1

Values of the Laser-Doppler signal (LDF) expressed in mV before and after treatment with PGE1 complexed with Phosphatidylcholine and administered through the T.E.B. route on penile areas for the treatment of impotence of vascular origin.

| Pat. No. | Initials | Age | Diagnosis | LDF Before | After |
|---|---|---|---|---|---|
| 1 | S. F. | 53 | Cavernous arteriovenous macro-microangiosclerosis | 60.55 | 225.03 |
| 2 | I. P. | 51 | Cavernous arterial macro-microvasculopathy | 17.55 | 136.2 |
| 3 | F. S. | 32 | Erectile dysfunction due to diabetic microangiopathy | 97.27 | 207.25 |
| 4 | F. G. | 55 | Arterial and cavernous macro-microangiopathy | 56.96 | 160.51 |
| 5 | B. G. | 40 | Cavernous arterial microangiopathy | 11.64 | 111.31 |
| 6 | C. G. | 29 | Microangiosclerotic tabagic erectile dysfunction | 30.94 | 103.57 |
| 7 | F. M. | 48 | Initial arterial hypertensive angiosclerosis | 53.16 | 80.21 |
| 8 | B. R. | 64 | Cavernous arterial macro- and microangiosclerosis | 13.11 | 43.12 |
| 9 | S. L. | 56 | Cavernous arterial microangiosclerosis | 48.22 | 58.88 |
| 10 | C. G. | 51 | Cavernous hypertensive arterial-sclerotic microangiopathy | 139.66 | 324.74 |
| 11 | G. A. | 49 | Cavernous veno-occlusive dysfunction | 116.63 | 453 |
| 12 | M. A. | 59 | Cavernous arterial microangiopathy | 42 | 81.16 |
| 13 | P. R. | 30 | Cavernous arterial microangiopathy | 22.09 | 52.01 |
| 14 | S. G. | 36 | Cavernous arterial microangiopathy | 37.62 | 78.8 |
| 15 | N. M. | 43 | Hypertensivecavernous arterial microangiopathy | 67.2 | 152.1 |
| Mean values ± S.D. | | | | 54.33 ± 37.69 | 153 ± 121.60 |
| Statistical significance | | | | | P = 0.005 |

A series of pharmacological tests clearly evidenced, with high statistical significance, the positive effects of the Troxerutine/Phosphatidylcholine complex on skin microcirculation.

Demonstration of the microvasculokinetic activity of the Phosphatidylcholine/Troxerutine complex in man is given in Table 2 that regards the contraction strength of the smooth muscle cells of the arteriolar media (sphygmicity, vasomotility: see Curri, S. B.: "Vasomotility, Sphygmicity and Vasomotion", Int. Symp. on Microcirculation, Rome, 10th Oct., 1991).

Table 2 Modification of the area of the sphygmic waves, expressed in $mm^2$, in a group of untreated controls and after 20, 40 and 60 minutes from topical application of a Phosphatidylcholine/Troxerutine complex at the dose of 5 ml (30 mg/ml)

| Groups | Area mm2 | Significance |
|---|---|---|
| Controls | 50.87 ± 11.5 | |
| after 20 min. | 79.71 ± 17 | P < 0.001 |
| after 40 min. | 106.6 ± 24.4 | P < 0.0001 |
| after 60 min. | 106.9 ± 23 | P < 0.0001 |

(from Curri et al. Art. Vein. XI, Oct. 1992, mod.)

The pharmaceutical or cosmetic composition referred to in this invention preferably include quantities between 01 and 20% in weight of the active principle having microvasculo-kinetic activity.

Advantageously and preferably, such compositions also include de-ionized sterile water, which by suitable stirring using appropriate mechanical devices give place to an aqueous lipoosomal microdispersion. Furthermore, such compositions include a pharmacologically inert excipient and are prepared in any administration form that is suitable for topical and epimucosal application on any surface of the body and on skin that is particularly thin and sensitive, such as that of the penis, i.e. in the form of cream, ointment, gel, emulsion and similar forms, prepared with traditional methods; and also urethral suppositories.

For the purposes of the invention, the pharmacologically inert excipients preferred are those reported in the "Remington Pharmaceutical Sciences Handbook", Hack Pubi. Co., N.Y., USA.

The compositions of this invention are mainly used in the following areas:

1. In the pharmaceutical field: for the topical treatment of pathological conditions deriving from insufficient local penile microcirculatory flow, such as erectile impotence or excessively short duration of erection, especially in subjects with early physiological senile involution of the arteries and arterioles; in patients with hypertension, particularly those undergoing treatment with beta-blockers; in diabetic patients, even in the absence of clinically evident manifestations of diabetic microangiopathy; in patients affected by vasculopathies of arterial-arteriolosclerotic origin, even in the absence of evident symptoms of central or peripheral vascular insufficiency; in patients affected by rheumatoid arthritis, with rheumatic microangiopathy, in whom among the symptoms related to the main disease there is a clinical condition of erectile impotence.
2. In cosmetology: for the treatment of penile areas that are considered "at risk", in which despite the absence of a clinically evident condition of impotence due to vascular causes, it is deemed appropriate to carry out prevention therapy to avoid the presumable evolution of the previously ascertained basic clinical condition. Furthermore, in the cases where occasional episodes of erectile impotence appear to indicate a possible deterioration in time of the contingent situations leading to permanent erectile impotence: this is the case of senile physiological involution of the macro and microvasculo-tissue system of erection.

Further characteristics and advantages of the invention are more evident in the following description of certain unrestrictive examples of pharmaceutical or cosmetic compositions according to the invention, whose microvasculo-kinetic effects and activity in increasing the speed and volume of penile blood flow directed towards the cavernous bodies can be observed by using suitable instrumental techniques.

EXAMPLE 2.1

A formulation with microvasculokinetic activity in the form of a "liposomal-like" aqueous microdispersion was prepared with known methods, having the following composition:
Each 10 ml Vial Contains:

| | |
|---|---|
| Complex of hydrodispersible Phosphatidylcholine purified from soya/Troxerutine | 100 mg |
| De-ionized sterile water q.s. to: | 10 ml |
| Vials prepared in a sterile environment | |

EXAMPLE 2.2

A formulation with penile microvasculokinetic activity in the form of a gel was prepared with known methods, having the following composition:
100 g of Gel Contain:

| | |
|---|---|
| Troxerutine complexed with Phosphatidylcholine purified from Soya | 5.0 g |
| Polyacrylamide | 5.0 g |
| Isoparaffin | 5.0 g |
| Laureth 7 | 5.0 g |
| Methyidibromo-glutaronitrile | 0.2 g |
| Phenoxyethanol | 0.2 g |
| Fragrance Cerizza 25670 | 0.2 g |
| De-ionized water q.s. to: | 100.0 g |

EXAMPLE 2.3

A formulation with penile microvasculokinetic activity in the form of a gel was prepared with known methods, having the following composition:
100 g of Gel Contain:

| | |
|---|---|
| Troxerutine complexed with Phosphatidylcholine | 10.0 g |
| Eichosapentaenoic acid 60% | 1.0 g |
| Volpo 20 (ethoxylated triglycerides C8–C12) | 7.5 g |
| Propyleneglycol | 20.0 g |
| Softigen 767 (polyoxyethylene-20-oleilether) | 20.0 g |
| Carboxyvinylpolymer | 1.5 g |
| Triethanolamine | 2.0 g |
| Imidazolidinylurea | 0.3 g |
| Methylparahydroxybenzoate | 0.1 g |
| De-ionized water q.s. to: | 100.0 g |

EXAMPLE 2.4

Experimental Comparative Data

In order to carry out an in vivo verification of the effects on cutaneous and glans penis microcirculation recently developed capillaroscopic techniques were used based on the Optic Probe Video-Capillaroscope, which for the first time enabled examination of the microvessels of the penis in normal and in pathological conditions, as well as other cutaneous or mucosal regions that to-date could not be reached for biomicroscopic exploration (S. B. Curri: *Min. Angiol* 1992, 17, suppl. 4, nr. 3, 43–51; ibid. 1993, 18.

suppl.2, n. 4, 38–43 and ibid. 159–165; S. B. Curri, *Artéres et Veines* 1994, vol. XIII, nr. special, 16–22; S. B. Curri, *Progr. Appl. Microcirc.*, Basel, Karger 1993, Vol. 20, 8–13; S. B. Curri, *Flebologia* 1992, 3/3, 247–259).

Visualization of the local microcirculatory system of penile skin and of the glans penis in vivo was carried out with a Video-Capillaroscope "Video-Microscope System, Scopeman MS 204, Japan", equipped with 200×(field depth: 1.6 mm) and 400×(field depth: 0.28 mm) contact lenses, devices for the automatic control of lighting (cold halogen light from a 100 W lamp), automatic calibration of the whiteness, for continuous regulation of brightness and selection of the filters. This Video-Capillaroscope elaborates an image captured through a lens placed in direct contact with the skin of the penis or with the glans penis, appropriately diaphanized with an immersion oil for microscopy, which is transmitted to a monitor through an optical fibre cable. The resulting capillaroscopic image is recorded on a videorecorder (Sony Video 8 Hi-Fi, Stereo Video GV-USE PAL) and then printed on special photographic paper with a video-printer having an image-holding function (Color-Video Printer VY-SS50, Hitachi, Japan), according to the description reported in: S. B. Curri, V Nat. Congress and IV Int. Congr., It. Soc. of Phlebology, Siena Sep. 27–30 1993, Abstr. in Min. Angiol., 1993, 18,36.

For the quantification of the area occupied by the capillaries of the dorsal and ventral areas of the penis and the glans penis, the Video-Capillaroscope was connected through a cable to a computerized image analysis system (EIZO-FLEXSCAN System, TTL Analog Multiple Scan, 15.5–38.5 Khz, Accorn Ltd., Cambridge, U.K.), equipped with suitable software from Foster-Findlay Ass., Ltd., Cambridge, U.K.

The capillaroscopic image of the microvessels of the penis (we repeat, for the first time in the history of microangiology and microcirculation) was in this way digitalized, thus enabling expression in numbers of pixels of both the total surface of the capillaroscopic field ("Total field Area"= TFA) and the area occupied by the microvessels of the penis ("Total Object Area"=TOA)—See Table 3.

Through this novel capillaroscopic technique it was therefore possible, by calculating the TFA/TOA ratio, to discover the "capillary density" (CD), corresponding to the area in pixels occupied by the microvessels perfused by blood flow present in the penile skin and the glans penis mucosa (see "%" column in Table 3).

The trial was performed on a group of 10 patients affected by impotence of vascular origin, aged between 34 and 62 years (mean 49±7.97), in whom the clinical condition was investigated also with instrumental methods (Eco-Color Doppler technique) able to indicate the anatomic-functional status of the left and right dorsal arteries of the penis.

The Video-Capillaroscopic observations were performed in the dorsal region of the penis, at baseline and after application of a preparation according to example No. 1.

Statistical analysis of the data was carried out with "Statgraphics Plus" software (Manugistic Inc., Bitstream Inc., Cambridge, Mass., USA).

In a second group of 5 patients, affected by impotence of vascular origin due to diastolic arterial hypertension, who were undergoing treatment with beta-blockers, after having performed the baseline controls and ascertained the degree of microcirculatory damage in the dorsal penile region using the Optic Probe Video-Capillaroscope, a long term treatment was undertaken for a minimum of two months with the formulation described under Example No. 1.

The admission criteria were the following:

1. no active erections during the last six months;
2. not more than 3–4 partial, incomplete erections during sleep at night or upon awakening, per month.

Treatment at the dose of 10 ml twice per day, mornings and evenings, was carried out as follows:

keeping the left hand cupped beneath the penis, with the glans penis uncovered, approximately 0.5 ml of the hydrodispersible complex are dripped on to the penile skin and the mucosa of the glans penis and massaged delicately with the right hand until the liquid is completely absorbed. This procedure is repeated until the whole contents of the 10 ml vial are used. The time required is approximately 4–6 minutes.

The clinical evaluation parameters were the following:

A. number of active erections per month
B. number of erections after night rest or upon awakening per month

TABLE 3

|       |        | NO.   | TFA   | TOA     | %     |
|-------|--------|-------|-------|---------|-------|
| Z.P.A. | BEFORE | no. 1 | 237   | 45793   | 2754.75 | 5.99 |
|       |        | no. 2 | 129   | 44693   | 3658.5  | 8.18 |
|       |        | no. 3 | 158   | 43232   | 2057.25 | 4.76 |
|       |        | no. 4 | 122   | 42147   | 2184.75 | 5.18 |
|       |        | no. 5 | 189   | 38986   | 3309    | 8.49 |
|       | AFTER  | no. 1 | 179   | 45120   | 2372.25 | 5.26 |
|       |        | no. 2 | 262   | 48555   | 4617.75 | 9.5  |
|       |        | no. 3 | 195   | 49276   | 3407.25 | 6.9  |
|       |        | no. 4 | 268   | 45360   | 2898.75 | 6.39 |
|       |        | no. 5 | 101   | 40309   | 1583.25 | 3.93 |
| P.G.  | BEFORE | no. 1 | 217   | 38304   | 3405    | 8.89 |
|       |        | no. 2 | 53    | 30816   | 1238.25 | 4.01 |
|       |        | no. 3 | 248   | 36240   | 2333.25 | 6.44 |
|       |        | no. 4 | 177   | 27178   | 1942.5  | 7.14 |
|       |        | no. 5 | 197   | 31605   | 2036.25 | 6.44 |
|       | AFTER  | no. 1 | 285   | 36792   | 3515.25 | 9.55 |
|       |        | no. 2 | 239   | 34808   | 2613    | 7.5  |
|       |        | no. 3 | 190   | 33516   | 3707.25 | 11.06 |
|       |        | no. 4 | 234   | 33810   | 4011    | 11.86 |
|       |        | no. 5 | 263   | 36058   | 3105    | 8.61 |
| P.A.  | BEFORE | no. 1 | 278   | 36456   | 1301.25 | 3.57 |
|       |        | no. 2 | 118   | 26607   | 2000.25 | 7.5  |
|       |        | no. 3 | 212   | 39215   | 1638    | 4.18 |
|       |        | no. 4 | 214   | 50547   | 1693.5  | 3.35 |
|       |        | no. 5 | 223   | 34368   | 1734.75 | 5.05 |
|       | AFTER  | no. 1 | 230   | 47188   | 3189    | 6.75 |
|       |        | no. 2 | 401   | 48694   | 5054.25 | 10.37 |
|       |        | no. 3 | 294   | 46376   | 2333.25 | 5.03 |
|       |        | no. 4 | 222   | 50094   | 2217.75 | 4.42 |
|       |        | no. 5 | 216   | 45974   | 2529    | 5.5  |
| A.U.  | BEFORE | no. 1 | 187   | 49530   | 2262    | 4.5  |
|       |        | no. 2 | 309   | 46552   | 2658    | 5.7  |
|       |        | no. 3 | 293   | 47058   | 2656.5  | 5.64 |
|       |        | no. 4 | 356   | 34119   | 2784.75 | 8.16 |
|       |        | no. 5 | 277   | 46872   | 3723    | 7.94 |
|       | AFTER  | no. 1 | 159   | 44704   | 2640    | 5.9  |
|       |        | no. 2 | 207   | 47244   | 3670.5  | 7.76 |
|       |        | no. 3 | 194   | 45825   | 4259.25 | 9.29 |
|       |        | no. 4 | 321   | 48006   | 3605.25 | 7.5  |
|       |        | no. 5 | 177   | 46366   | 4182    | 9.02 |
| T.R.  | BEFORE | no. 1 | 97    | 31652   | 1761.75 | 5.56 |
|       |        | no. 2 | 339   | 48514   | 3939.75 | 8.12 |
|       |        | no. 3 | 217   | 47250   | 4473.75 | 9.46 |
|       |        | no. 4 | 89    | 37636   | 3365.25 | 8.94 |
|       |        | no. 5 | 202   | 47564   | 3783.75 | 7.95 |
|       | AFTER  | no. 1 | 261   | 46228   | 3957    | 8.55 |
|       |        | no. 2 | 255   | 46872   | 4350.75 | 9.28 |
|       |        | no. 3 | 272   | 48514   | 6675.75 | 13.76 |
|       |        | no. 4 | 202   | 44750   | 6319.5  | 14.12 |
|       |        | no. 5 | 158   | 40584   | 5554.5  | 6.68 |
| T.M.  | BEFORE | no. 1 | 277   | 45980   | 4787.25 | 10.41 |
|       |        | no. 2 | 187   | 32308   | 2405.25 | 7.44 |
|       |        | no. 3 | 160   | 35126   | 3748.5  | 10.67 |

TABLE 3-continued

|   |   |   | NO. | TFA | TOA | % |
|---|---|---|---|---|---|---|
|  |  | no. 4 | 237 | 33033 | 3805.5 | 11.52 |
|  |  | no. 5 | 191 | 36660 | 4643.25 | 12.66 |
|  | AFTER | no. 1 | 376 | 46624 | 5859 | 12.56 |
|  |  | no. 2 | 191 | 41904 | 4407 | 10.51 |
|  |  | no. 3 | 280 | 47970 | 3944.25 | 8.22 |
|  |  | no. 4 | 292 | 34104 | 5533.5 | 16.22 |
|  |  | no. 5 | 237 | 42423 | 3752.25 | 8.84 |
| T.R. 2 | BEFORE | no. 1 | 229 | 40950 | 3196.5 | 7.8 |
|  |  | no. 2 | 202 | 38793 | 2434.5 | 6.27 |
|  |  | no. 3 | 233 | 26469 | 1907.25 | 7.2 |
|  |  | no. 4 | 172 | 25800 | 2094 | 8.12 |
|  |  | no. 5 | 144 | 16932 | 1982.25 | 11.7 |
|  | AFTER | no. 1 | 461 | 45741 | 3686.25 | 8.05 |
|  |  | no. 2 | 551 | 47752 | 3684 | 7.71 |
|  |  | no. 3 | 466 | 48250 | 5974.5 | 12.38 |
|  |  | no. 4 | 189 | 40132 | 2938.5 | 7.32 |
|  |  | no. 5 | 405 | 46046 | 4771.5 | 10.36 |
| G.G. | BEFORE | no. 1 | 337 | 46299 | 3200.25 | 6.91 |
|  |  | no. 2 | 298 | 46470 | 3981 | 8.56 |
|  |  | no. 3 | 339 | 45682 | 2749.5 | 6.01 |
|  |  | no. 4 | 372 | 48006 | 3546 | 7.38 |
|  |  | no. 5 | 407 | 47564 | 5610 | 11.79 |
|  | AFTER | no. 1 | 356 | 46314 | 3729 | 8.05 |
|  |  | no. 2 | 331 | 46000 | 4418.25 | 9.6 |
|  |  | no. 3 | 192 | 32697 | 3581.25 | 10.95 |
|  |  | no. 4 | 295 | 40608 | 3531 | 8.69 |
|  |  | no. 5 | 207 | 36480 | 3255.75 | 8.92 |
| C.V. | BEFORE | no. 1 | 341 | 34944 | 2715 | 7.76 |
|  |  | no. 2 | 377 | 42846 | 3345 | 7.8 |
|  |  | no. 3 | 364 | 44652 | 3462.75 | 7.75 |
|  |  | no. 4 | 286 | 44454 | 2997.75 | 6.74 |
|  |  | no. 5 | 105 | 47058 | 2278.5 | 4.84 |
|  | AFTER | no. 1 | 318 | 37636 | 2261.25 | 6 |
|  |  | no. 2 | 443 | 41860 | 4405.5 | 10.52 |
|  |  | no. 3 | 324 | 44196 | 5125.5 | 11.59 |
|  |  | no. 4 | 392 | 45162 | 4861.5 | 10.76 |
|  |  | no. 5 | 311 | 28028 | 4314.75 | 15.39 |
| P.M. | BEFORE | no. 1 | 343 | 42672 | 3577.5 | 5.38 |
|  |  | no. 2 | 431 | 45684 | 4317 | 9.45 |
|  |  | no. 3 | 213 | 28028 | 2628 | 9.38 |
|  |  | no. 4 | 303 | 32754 | 3358.5 | 10.25 |
|  |  | no. 5 | 193 | 27722 | 2786.25 | 10.05 |
|  | AFTER | no. 1 | 158 | 32130 | 4122 | 12.83 |
|  |  | no. 2 | 291 | 41109 | 5451 | 13.26 |
|  |  | no. 3 | 138 | 31313 | 3706.5 | 11.84 |
|  |  | no. 4 | 269 | 34692 | 4332 | 12.49 |
|  |  | no. 5 | 293 | 38592 | 6508.5 | 16.86 |

RESULTS

Table 3 reports the results obtained at baseline and 60 minutes after application of 5 ml of the preparation described under Example No. 1, on the penile skin and on the glans penis.

The data indicate that topical and epimucosal administration of the invention directly onto the skin of the penis and the glans penis, causes a statistically significant increase of microcirculatory flow in the penis, that is very evident in patients affected by erectile impotence in whom there is a constant deficiency of arterial-arteriolar blood flow at baseline.

Chronic topical treatment, for not less than two-three months, with 10 ml twice per day of the invention described under Example No. 1, applied in small quantities and massaged until completely absorbed by the penile skin, results in a substantial improvement of the clinical baseline condition.

In particular, there was a substantial increase in the frequency of spontaneous morning erections, which in many patients had been almost non-existent at baseline; a longer duration of the erections to enable normal and satisfactory sexual intercourse; and a remarkable increase in the number of monthly erections from libido. Upon pathogenetic evaluation of the causes, these clinical aspects appear strictly correlated with the improved penile microcirculation induced by administration of the microvasculo-kinetic drug applied topically.

The following table reports the trend of the clinical parameters registered after long term treatment (2 months) with the formulation described under Example No. 1, in the second group of patients (see Example No. 4, "Experimental Comparative Data"):

TABLE 4

Trend of the clinical parameters after two months' treatment with the formulation under Example 2.1, at the dose of 10 ml twice per day, in patients with erectile impotence of vascular origin due to hypertensive penile microangiopathy.

| | | | NO. OF ERECTIONS AFTER NIGHT REST AND UPON AWAKENING | | NUMBER OF ACTIVE ERECTIONS PER MONTH | |
|---|---|---|---|---|---|---|
| PAT. NO. | INITIALS | AGE | Before | After | Before | After |
| 1 | S. G. | 55 | 0 | 8 | 0 | 6 |
| 2 | M. B. | 57 | 0 | 10 | 0 | 13 |
| 3 | C. G. | 50 | 2 | 20 | 0 | 18 |
| 4 | A. A. | 52 | 6 | 14 | 0 | 12 |
| 5 | M. G. | 50 | 0 | 4 | 0 | 4 |

Table 4 clearly indicates the efficacy of the treatment.

The novelty, therefore, consists in the opportunity to adopt a different therapeutical approach from normal andrological practice which, as is known, involves intracavernous injection of active principles and/or vasodilators, in order to handle the complex microvascular-tissue condition that is at the basis of erectile impotence caused by insufficient arterial-arteriolar blood flow, particularly as regards the evident and ubiquitous microvascular pathologies such as for example, arterial hypertension, diabetes, arteriolosclerosis.

Markedly, one of the unrecognized and unreported problems among the undesired side effects of treatment with beta-blockers for arterial hypertension, is the appearance, after approximately 1–3 years from starting treatment, of a progressive decrease of erections, in some cases up to complete disappearance, both spontaneous and from libido. As far as the application termed "cosmetic" is concerned (see above), the novelty of the invention assumes remarkable practical interest with basically preventive objectives in patients who are defined "at risk", such as those who suffer from hypertension.

I claim:

1. A method for causing a penis to swell to erection by increasing sphygmic activity of small arteries of the penis, the method comprising:

(a) providing a topical pharmaceutical composition, the composition comprising 3-O-β-hydroxy ethyl-rutoside (Troxerutine) and purified Phosphatidylcholine, wherein the 3-O-β-hydroxyethyl-rutoside (Troxerutine) forms a liposomal physical-chemical complex with the purified Phosphatidylcholine; and (b) applying the topical pharmaceutical composition topically onto skin of the penis, whereby the pharmaceutical composition increases the sphygmic activity of the small arteries of the penis and causes the penis to swell to erection.

2. A method as claimed in claim 1, wherein the complex comprises from 1 to 15% by weight of the composition.

3. A method as claimed in claim 2, wherein the composition is an aqueous liposomal microdispersion, gel, ointment, cream, or emulsion.

4. A method as claimed in claim 3, wherein the composition further comprises at least one excipient that is pharmacologically acceptable.

5. A method as claimed in claim 1, wherein the composition is an aqueous microdispersion or a gel, the complex constituting approximately 1% by weight of the composition when the composition is an aqueous microdispersion, the complex constituting approximately 5–10% by weight of the composition when the composition is a gel.

6. A method as claimed in claim 2, wherein the penis has a glans, and wherein step (b) comprises applying the topical pharmaceutical composition topically onto skin of the glans of the penis.

7. A method as claimed in claim 2, wherein step (b) comprises applying the topical pharmaceutical composition topically onto skin of the penis twice daily for at least two months.

8. A method as claimed in claim 3, wherein the composition is the aqueous liposomal microdispersion, and wherein step (b) comprises applying 10 ml. of the aqueous liposomal microdispersion topically onto skin of the penis twice daily for at least two months.

9. A method as claimed in claim 2, wherein the 3-O-β-hydroxyethyl-rutoside (Troxerutine) and the Phosphatidylcholine are complexed in a molar ratio of 2:1.

10. A method as claimed in claim 5, wherein the penis has a glans, and wherein step (b) comprises applying the topical pharmaceutical composition topically onto skin of the penis daily for at least two months.

11. A method as claimed in claim 2, wherein the penis has a glans, and wherein step (b) comprises applying the topical pharmaceutical composition topically onto skin of the penis daily for at least two months.

12. A method as claimed in claim 1, wherein the composition is an aqueous liposomal microdispersion, gel, ointment, cream, or emulsion.

13. A method as claimed in claim 1, wherein the composition further comprises at least one excipient that is pharmacologically acceptable.

14. A method as claimed in claim 4, wherein the composition is an aqueous microdispersion or a gel, the complex constituting approximately 1% by weight of the composition when the composition is an aqueous microdispersion, the complex constituting approximately 5–10% by weight of the composition when the composition is a gel.

15. A method as claimed in claim 1, wherein the 3-O-β-hydroxyethyl-rutoside (Troxerutine) and the Phosphatidylcholine are complexed in a molar ratio of 2:1.

16. A method as claimed in claim 3, wherein the 3-O-β-hydrexyethyl-rutoside (Troxerutine) and the Phosphatidylcholine are complexed in a molar ratio of 2:1.

17. A method as claimed in claim 4, wherein the 3-O-β-hydroxyethyl-rutoside (Troxerutine) and the Phosphatidylcholine are complexed in a molar ratio of 2:1.

18. A method as claimed in claim 5, wherein the 3-O-β-hydroxyethyl-rutoside (Troxerutine) and the Phosphatidylcholine are complexed in a molar ratio of 2:1.

19. A method as claimed in claim 1, wherein the penis has a glans, and wherein step (b) comprises applying the topical pharmaceutical composition topically onto skin of the glans of the penis.

20. A method as claimed in claim 1, wherein the penis has a glans, and wherein step (b) comprises applying the topical pharmaceutical composition topically onto skin of the penis daily for at least two months.

* * * * *